United States Patent [19]
Ikawa et al.

[11] Patent Number: 5,719,298
[45] Date of Patent: Feb. 17, 1998

[54] METHODS OF PRODUCING PANTOTHENIC ACID DERIVATIVE AND ITS STARTING MATERIALS FOR PRODUCING THE SAME

[75] Inventors: Hiroshi Ikawa, Tokyo; Hajime Matsumoto, Hachiohji, both of Japan

[73] Assignee: Fujirebio Inc., Tokyo, Japan

[21] Appl. No.: 445,720

[22] Filed: May 22, 1995

Related U.S. Application Data

[62] Division of Ser. No. 199,939, Feb. 22, 1994, abandoned.

[30] Foreign Application Priority Data

| | | | |
|---|---|---|---|
| Feb. 23, 1993 | [JP] | Japan | 5-056324 |
| Feb. 23, 1993 | [JP] | Japan | 5-056325 |
| Feb. 23, 1993 | [JP] | Japan | 5-056326 |
| Apr. 15, 1993 | [JP] | Japan | 5-111167 |

[51] Int. Cl.$^6$ .......................... C07D 319/06; C07C 251/04
[52] U.S. Cl. .......................... 549/372; 564/272; 564/275; 564/278; 564/391; 564/397; 564/398
[58] Field of Search .......................... 549/372; 564/272, 564/275, 278, 391, 397, 398

[56] References Cited

U.S. PATENT DOCUMENTS 5,120,738  6/1992  Ikawa et al. .......................... 514/255

*Primary Examiner*—Joseph McKane
*Attorney, Agent, or Firm*—Oblon, Spivak, McClelland, Maier & Neustadt, P.C.

[57] ABSTRACT

A method of producing a pantothenic acid derivative of formula (I):

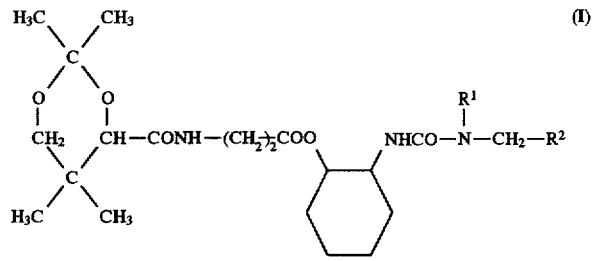

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, is provided, including methods of producing the starting materials for producing the same and novel amine derivative that can be used for the production of the pantothenic acid derivative.

7 Claims, No Drawings

METHODS OF PRODUCING PANTOTHENIC ACID DERIVATIVE AND ITS STARTING MATERIALS FOR PRODUCING THE SAME

This is a division of application Ser. No. 08/199,939 filed on Feb. 22, 1994 now abandoned.

BACKGROUND OF THE INVENTION

1. Field of the Invention

The present invention relates to methods of producing a pantothenic acid derivative and starting materials for producing the pantothenic acid derivative, more particularly to a method of producing a pantothenic acid derivative which is known as having excellent inhibition activity exerting on Acyl CoA-Cholesterol-Acyltransferase (hereinafter referred to as "ACAT"), and the effect of reducing the amount of lipids in the blood, and a method of producing a pantothenic acid acetonide which is a starting material for producing the above-mentioned pantothenic acid derivative, and a method of producing a urea derivative which is another starting material for producing the above-mentioned pantothenic acid derivative.

The present invention also relates to a novel amine derivative that can be used as a starting material for producing the urea derivative and to a method of producing the novel amine derivative.

2. Discussion of Background

Conventionally, a pantothenic acid derivative of the following formula (I) is produced by allowing a carboxylic acid derivative to react with an alcohol derivative in the presence of a carbodiimide derivative or the like which serves as a condensation agent to form an ester bond as disclosed in Japanese Laid-Open Patent Application 3-218340:

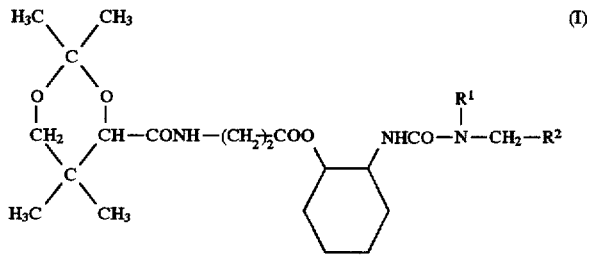

wherein each of $R^1$ and $R^2$ is different, and is a branched aliphatic hydrocarbon group having 3 to 5 carbon atoms or a phenyl group; or a straight chain aliphatic hydrocarbon group having 5 to 10 carbon atoms.

The above-mentioned conventional method using a carbodiimide derivative, however, has the shortcomings that the yield of the pantothenic acid derivative is because of the formation of side products, and a large amount of a urea derivative which must be eliminated by a very complicated process is formed in the course of the reaction. Therefore, this is not a suitable industrial method for producing the pantothenic acid derivative.

A pantothenic acid acetonide with the following formula (II), which serves as a starting material for producing the above-mentioned pantothenic acid derivative, is conventionally produced, for instance, by a method comprising the steps of performing benzylation of the carboxylic group of calcium pantothenate to produce benzyl pantothenate, allowing benzyl pantothenate to react acetone under an acidic condition to produce pantothenic acid acetonide benzyl ester, and subjecting the benzyl group thereof to hydrolysis or hydrogenolysis as disclosed in Japanese Laid-Open Patent Application 3-218366:

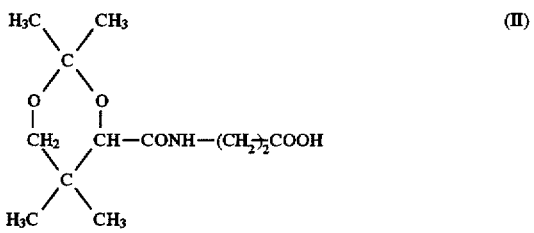

The above-mentioned method, however, has the shortcomings that complicated steps such as protection and deprotection of carboxylic group are included, the yield of the pantothenic acid acetonide is low, and a large amount of side products have to be removed from the reaction mixture.

Therefore, this conventional method is not a satisfactory industrial method for producing the pantothenic acid acetonide.

A urea derivative with the following formula (III) is another starting material for producing the above-mentioned pantothenic acid derivative:

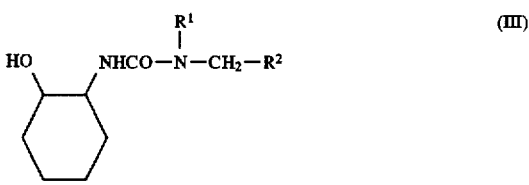

wherein each of $R^1$ and $R^2$ is different, and is a branched aliphatic hydrocarbon group having 3 to 5 carbon atoms, or a straight chain aliphatic hydrocarbon group having 5 to 10 carbon atoms.

The above urea derivative of formula (III) is conventionally produced, for instance, by any of the following two methods:

Method 1: An isocyanate derivative, which is derived from a carboxylic acid derivative such as carboxylic acid, acid amide, or acid azide, is allowed to react with an amine compound.

Method 2: An amine compound is allowed to react with phosgene or carbon monoxide.

In order to produce the urea derivative of formula (III), it is extremely difficult to efficiently synthesize 2-hydroxycyclohexane carboxylic acid which serves as a starting material for producing the urea derivative in the above-mentioned Method 1, and the selectivity of the reaction of 2-hydroxycyclohexyl isocyanate with the following amine derivative of formula (IV) is low:

wherein $R^1$ and $R^2$ are respectively the same as defined previously in formula (I).

In Method 2, a special apparatus is required for handling phosgene or carbon monoxide, which must be handled with the utmost care.

Therefore, the above-mentioned Methods 1 and 2 are not suitable for industrial production of the urea derivative of formula (III).

Conventionally, secondary amine compounds are widely used as starting materials for producing a variety of medicines, drugs and agricultural chemicals. However, secondary amine compounds with two aliphatic hydrocarbon groups bonded to amino group being different, and at least one of the two aliphatic hydrocarbon groups being an aliphatic hydrocarbon group having 5 or more carbon atoms, have not been reported yet.

In particular, the amine derivative of the previously mentioned formula (IV) which is capable of serving as a starting material for producing the above-mentioned urea derivative of formula (III) has not been reported yet:

(IV)

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms.

Conventionally secondary amine compounds are prepared by any of the following methods:

Method 1: A primary amine is allowed to react with a compound with a halogenated alkyl group.

Method 2: A primary amine is allowed to react with a carboxylic acid halide to obtain an amide compound, and the thus obtained amide is then reduced.

However, when the above-mentioned amine derivative of formula (IV) is prepared by Method 1, in which a compound with a halogenated alkyl group is used, tertiary amines and quaternary ammonium salts are produced as side products, so that the yield of the amine derivative is low and complicated steps are required for isolating the desired amine derivative from the reaction mixture and purifying the same.

Furthermore, when the above-mentioned amine derivative of formula (IV) is prepared by Method 2, a reducing agent which is not suitable for synthesizing a large amount of the desired amine derivative has to be used.

Therefore none of the above-mentioned Methods 1 and 2 is suitable for producing the amine for industrial use.

SUMMARY OF THE INVENTION

It is therefore a first object of the present invention to provide a method of producing a pantothenic acid derivative of the following formula (I):

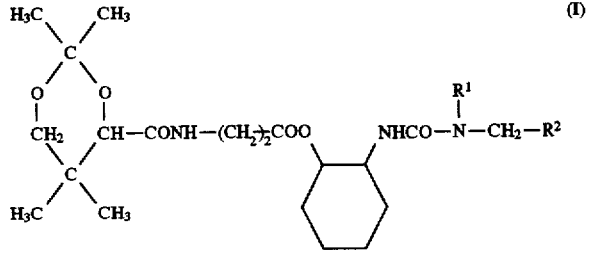
(I)

wherein each of $R^1$ and $R^2$ is different, and is a branched aliphatic hydrocarbon group having 3 to 5 carbon atoms, or a straight chain aliphatic hydrocarbon group having 5 to 10 carbon atoms.

A second object of the present invention is to provide a method of producing a pantothenic acid acetonide of the following formula (II), which serves as a starting material for producing the above-mentioned pantothenic acid derivative of formula (I):

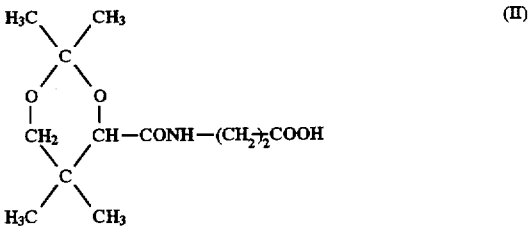
(II)

A third object of the present invention is to provide a urea derivative of the following formula (III), which serves as another starting material for producing the above-mentioned pantothenic acid derivative of formula (I):

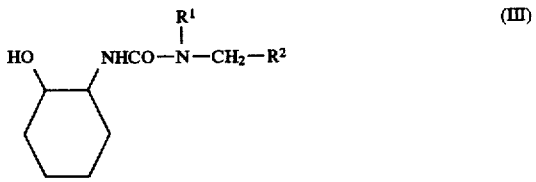
(III)

wherein $R^1$ and $R^2$ are respectively the same as defined previously in formula (I).

A fourth object of the present invention is to provide a method of producing the above-mentioned urea derivative of formula (III).

A fifth object of the present invention is to provide an amine derivative of formula (IV) that can be employed as a starting material for producing the urea derivative of formula (III):

$$R^1-N-CH_2-R^2$$
(with H above N)
(IV)

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms.

A sixth object of the present invention is to provide a method of producing the above-mentioned amine derivative of formula (IV).

A seventh object of the present invention is to provide an imine compound of formula (XII),

(XII)

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, which is an intermediate to be produced when producing the above-mentioned amine derivative of formula (IV).

An eighth object of the present invention is to provide a method of producing the imine compound of formula (XII).

The first object of the present invention is achieved by allowing the above-mentioned pantothenic acid acetonide of formula (II) to react with the urea derivative of formula (III) in the presence of a halogenating agent or an acylating agent.

The second object of the present invention is achieved by allowing a pantothenic acid compound of formula (V) to react with a dialkoxypropane derivative of formula (VI) in accordance with the following reaction scheme:

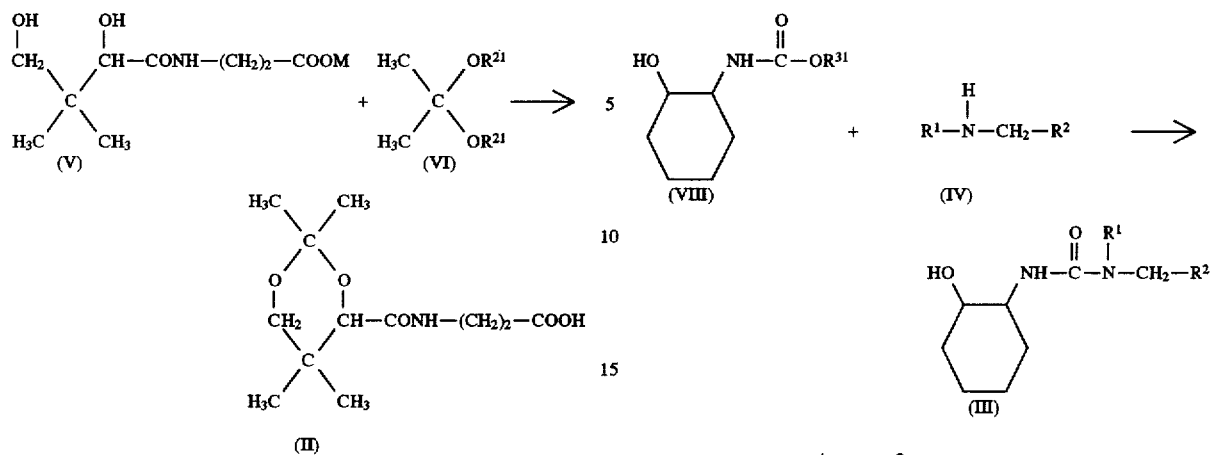

wherein M is a hydrogen atom, an alkali metal or an alkali earth metal, and $R^{21}$ is an alkyl group having 1 to 3 carbon atoms.

Alternatively, the second object of the present invention is achieved by allowing a pantothenic acid compound of formula (V) to react with a dialkoxypropene derivative of formula (VII) in accordance with the following reaction scheme:

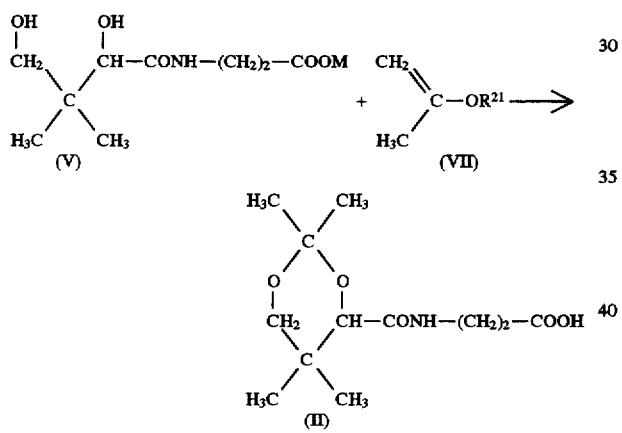

wherein M is a hydrogen atom, an alkali metal or an alkali earth metal, and $R^{21}$ is an alkyl group having 1 to 3 carbon atoms.

The third object of the present invention is achieved by a urea derivative with the following formula (III):

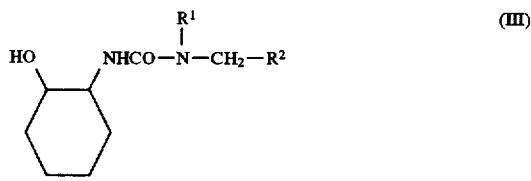

wherein each of $R^1$ and $R^2$ is different, and is a branched aliphatic hydrocarbon group having 3 to 5 carbon atoms, or a straight chain aliphatic hydrocarbon group having 5 to 10 carbon atoms.

The fourth object of the present invention is achieved by allowing a cyclohexanol derivative of formula (VIII) to react with the amine derivative of formula (IV) in accordance with the following reaction scheme:

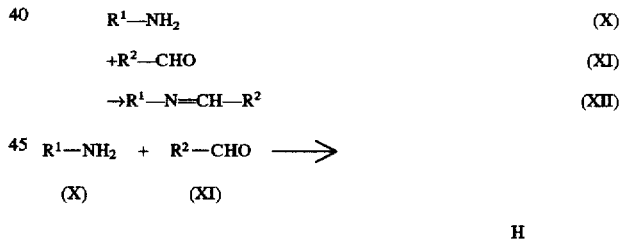

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, and $R^{31}$ is a phenyl group, a 4-nitrophenyl group, or a 2,4-dinitrophenyl group.

The fifth object of the present invention is achieved by an amine derivative of the following formula (IV):

$$\begin{array}{c} H \\ | \\ R^1-N-CH_2-R^2 \end{array} \quad (IV)$$

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms.

The sixth object of the present invention is achieved by a method comprising the steps of (a) allowing a primary amine of formula (X) to react with an aldehyde derivative of formula (XI) to produce an imine derivative of formula (XII), and (b) reducing the imine derivative in accordance with the following reaction scheme:

$$R^1-NH_2 \quad (X)$$
$$+R^2-CHO \quad (XI)$$
$$\rightarrow R^1-N=CH-R^2 \quad (XII)$$

$$R^1-NH_2 \; + \; R^2-CHO \longrightarrow$$
$$(X) \quad\quad\quad (XI)$$

$$R^1-N=CH-R^2 \xrightarrow{\text{Reduction}} \begin{array}{c} H \\ | \\ R^1-N-CH_2-R^2 \end{array}$$
$$(XII) \quad\quad\quad\quad (IV)$$

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms.

The seventh object of the present invention is achieved by an imine derivative of the following formula (XII), $$R^1-N=CH-R^2 \quad (XII)$$

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, which is an intermediate to be produced when producing the above-mentioned amine derivative of formula (IV).

The eighth object of the present invention is achieved by a method of producing the imine compound of formula (XII) comprising the step of allowing the previously mentioned primary amine of formula (X) to react with the previously mentioned aldehyde derivative of formula (XI).

DETAILED DESCRIPTION OF THE PREFERRED EMBODIMENTS

According to the present invention, a pantothenic acid derivative of formula (I) is produced by allowing a pantothenic acid acetonide of formula (II) to react with a urea derivative of formula (III) in the presence of a halogenating agent or an acylating agent in accordance with the following reaction scheme:

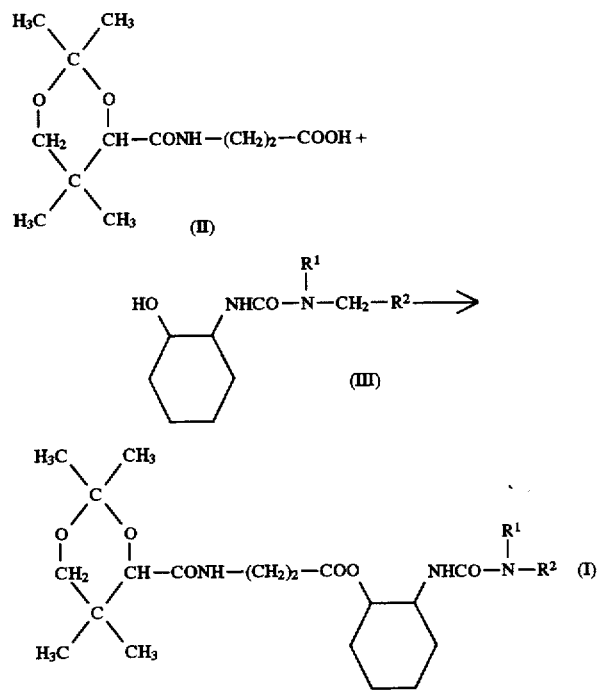

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms.

Examples of the halogenating agent for use in the above reaction are inorganic halogenating agents such as thionyl chloride, sulfuryl chloride, phosphorus pentachloride, phosphorus oxychloride, and phosphorus trichloride; and an acylating agent of formula (XIII), RX, wherein R is benzenesulfonyl group, p-toluenesulfonyl group, methanesulfonyl group, ethoxycarbonyl group, or phenoxycarbonyl group, and X is a chlorine atom, a bromine atom, or an iodine atom.

Specific examples of the acylating agent of formula (XIII) are benzenesulfonyl chloride, benzenesulfonyl bromide, benzenesulfonyl iodide, p-toluenesulfonyl chloride, p-toluenesulfonyl iodide, methanesulfonyl chloride, methanesulfonyl iodide, ethyl chloroformate, and phenyl chloroformate.

The urea derivative of formula (III), which is another starting material for producing the pantothenic acid-derivative of formula (I) can be produced from an industrially available starting material.

Specific examples of the urea derivative of formula (III) are as follows:

2-(3-neopentyl-3-pentylureido)cyclohexanol,
2-(3-hexyl-3-neopentylureido)cyclohexanol,
2-(3-heptyl-3-neopentylureido)cyclohexanol,
2-(3-octyl-3-neopentylureido)cyclohexanol,
2-(3-neopentyl-3-nonylureido)cyclohexanol,
2-(3-decyl-3-neopentylureido)cyclohexanol,
2-(3-isoproyl-3-pentylureido)cyclohexanol,
2-(3-hexyl-3-isopropylureido)cyclohexanol,
2-(3-heptyl-3-isopropylureido)cyclohexanol,
2-(3-isopropyl-3-octylureido)cyclohexanol,
2-(3-isopropyl-3-nonylureido)cyclohexanol,
2-(3-decyl-3-isopropylureido)cyclohexanol,
2-(3-isopropyl-3-undecylureido)cyclohexanol,
2-(3-benzyl-3-pentylureido)cyclohexanol,
2-(3-benzyl-3-hexylureido)cyclohexanol,
2-(3-benzyl-3-heptylureido)cyclohexanol,
2-(3-benzyl-3-octylureido)cyclohexanol,
2-(3-benzyl-3-nonylureido)cyclohexanol,
2-(3-benzyl-3-decylureido)cyclohexanol,
2-(3-t-butyl-3-pentylureido)cyclohexanol,
2-(3-t-butyl-3-hexylureido)cyclohexanol,
2-(3-t-butyl-3-heptylureido)cyclohexanol,
2-(3-t-butyl-3-octylureido)cyclohexanol,
2-(3-t-butyl-3-nonylureido)cyclohexanol, and
2-(3-t-butyl-3-decylureido)cyclohexanol.

Of the above-mentioned urea derivatives, the following optical active urea derivatives are particularly preferable for use in the present invention:

(1S, 2S)-2-(3-neopentyl-3-pentylureido)cyclohexanol,
(1S, 2S)-2-(3-hexyl-3-neopentylureido)cyclohexanol,
(1S, 2S)-2-(3-heptyl-3-neopentylureido)cyclohexanol,
(1S, 2S)-2-(3-octyl-3-neopentylureido)cyclohexanol,
(1S, 2S)-2-(3-neopentyl-3-nonylureido)cyclohexanol,
(1S, 2S)-2-(3-decyl-3-neopentylureido)cyclohexanol,
(1S, 2S)-2-(3-isoproyl-3-pentylureido)cyclohexanol,
(1S, 2S)-2-(3-hexyl-3-isopropylureido)cyclohexanol,
(1S, 2S)-2-(3-heptyl-3-isopropylureido)cyclohexanol,
(1S, 2S)-2-(3-isopropyl-3-octylureido)cyclohexanol,
(1S, 2S)-2-(3-isopropyl-3-nonylureido)cyclohexanol,
(1S, 2S)-2-(3-decyl-3-isopropylureido)cyclohexanol,
(1S, 2S)-2-(3-isopropyl-3-undecylureido)cyclohexanol,
(1S, 2S)-2-(3-benzyl-3-pentylureido)cyclohexanol,
(1S, 2S)-2-(3-benzyl-3-hexylureido)cyclohexanol,
(1S, 2S)-2-(3-benzyl-3-heptylureido)cyclohexanol,
(1S, 2S)-2-(3-benzyl-3-octylureido)cyclohexanol,
(1S, 2S)-2-(3-benzyl-3-nonylureido)cyclohexanol,
(1S, 2S)-2-(3-benzyl-3-decylureido)cyclohexanol,
(1S, 2S)-2-(3-t-butyl-3-pentylureido)cyclohexanol,
(1S, 2S)-2-(3-t-butyl-3-hexylureido)cyclohexanol,
(1S, 2S)-2-(3-t-butyl-3-heptylureido)cyclohexanol,
(1S, 2S)-2-(3-t-butyl-3-octylureido)cyclohexanol,
(1S, 2S)-2-(3-t-butyl-3-nonylureido)cyclohexanol, and
(1S, 2S)-2-(3-t-butyl-3-decylureido)cyclohexanol.

It is preferable the above reaction be carried out in a solvent. Examples of a solvent suitable for use in the above reaction are aliphatic hydrocarbons such as pentane, hexane, and heptane; aromatic hydrocarbons such as benzene, toluene, and xylene; ethers such as ethyl ether, tetrahydrofuran, and dioxane; and esters such as ethyl acetate and methyl acetate. These solvents can be used alone or in combination.

The reaction can be carried out at temperatures in the range of −30° C. to 120° C. but it is preferable that the reaction be carried out at temperatures in the range of 0° to 50° C. in order to perform the reaction efficiently.

Furthermore, in order to increase the efficiency of the reaction, it is preferable that the reaction be carried out in the presence of a base.

Specific examples of such a base for use in the above reaction are an organic base such as 4,4-dimethylaminopyridine, pyridine, collidine, DABCO, and triethylamine.

These bases can be used either alone or in combination. It is preferable that the amount of such a base be in the range of 0.5 to 5.0 equivalents to one equivalent of the urea derivative of formula (III).

EXAMPLE 1

[Preparation of (1S, 2S)-2-[3-(2,2-dimethylpropyl)-3-nonylureido]cyclohexane-1-yl 3-[N-(2,2,5,5-tetramethyl-1, 3-dioxane-4-carbonyl)amino] propionate]

The reaction scheme for this preparation was as follows:

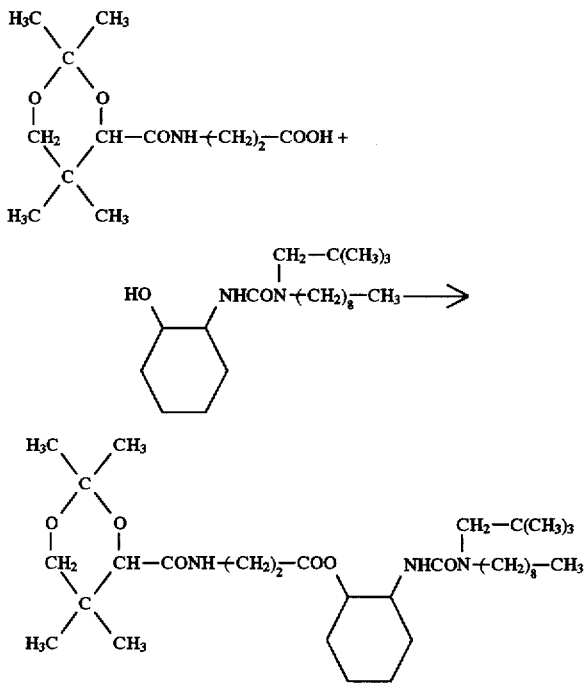

6.53 g (0.025 mol) of pantothenic acid acetonide (3-[N-(2,2,5,5-tetramethyl-1,3-dioxane-4-carbonyl)amino]-propionate), 7.45 g (0.021 mol) of (1S, 2S)-2-(3-neopentyl-3-nonylureido)cyclohexanol, and 7.70 g (0.063 mol) of 4,4-dimethylaminopyridine were dissolved in 300 ml of ethyl acetate. To this solution, 50 ml of an ethyl acetate solution containing 6.01 g (0.031 mol) of p-toluenesulfonyl chloride was added with stirring at room temperature. The mixture was stirred at room temperature for 6 hours.

A precipitate liberated from the reaction mixture was filtered out. An organic layer was separated from the filtrate, and was successively washed with a 1N-hydrochloride, water three times, a saturated aqueous solution of sodium bicarbonate, water three times, and a saturated aqueous solution of sodium chloride, and was then dried with anhydrous sulfuric sulfate.

The solvent was distilled away from the organic layer to obtain a residue. The residue was dissolved in hexane and crystallized with stirring, whereby (1S, 2S)-2-[3-(2,2-dimethylpropyl)-3-nonylureido]cyclohexane-1-yl 3-[N-(2,2,5,5-tetramethyl-1, 3-dioxane-4-carbonyl)amino] propionate] was obtained in a yield of 11.8 g (94%).

Melting point: 77.1°–79.4° C.

$^1$H-NMR(δ, CDCl$_3$): 0.88(3H, t, J=7 Hz), 0.91(9H, s), 0.96(3H, s), 1.04(3H, s), 1.05–2.21(22H, m), 1.42(3H, s), 1.47(3H, s), 2.43–2.62(2H, m), 2.91(1H, d, J=15 Hz), 2.97–3.10(1H, m), 3.05(1H, d, J=15 Hz), 3.16–3.27(1H, m), 3.28(1H, d, J=12 Hz), 3.37–3.64(2H, m), 3.69(1H, J=12 Hz), 3.71–3.86(1H, m), 4.08(1H, s), 4.52(1H, d, J=8 Hz), 4.70 (1H, ddd, J=11, 11, 4 Hz), 6.92(1H, t, J=5 Hz)

IR(v, KBr): 3388, 2932, 1730, 1670, 1618, 1378, 1098 cm$^{-1}$

Elemental analysis: Based on Molecular Formula $C_{33}H_{61}N_3O_6$

|  | % C | % H | % N |
|---|---|---|---|
| Calculated: | 66.52 | 10.32 | 7.05 |
| Found: | 66.26 | 10.55 | 7.30 |

Mass spectrometric analysis: (m/z, %): 595 (M+, 1.0)

Specific rotary power: $[\alpha]_D$=+32.33° (c 1.005, CHCl$_3$)

The pantothenic acid acetonide of formula (II) for use as a starting material for producing the above-mentioned pantothenic acid derivative of formula (I) is prepared by allowing a pantothenic acid compound of formula (V) to react with a dialkoxypropane derivative of formula (VI) in accordance with the following reaction scheme:

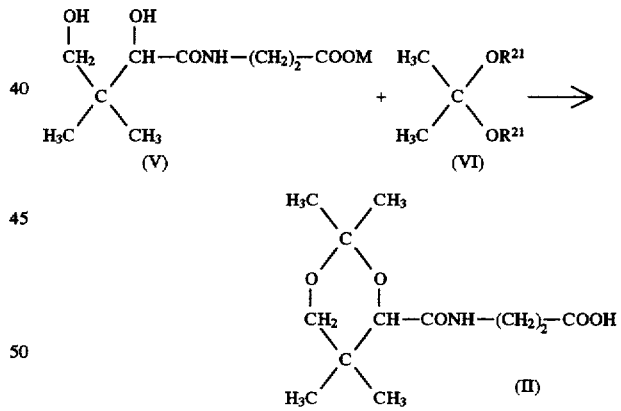

wherein M is a hydrogen atom, an alkali metal or an alkali earth metal, and R$^{21}$ is an alkyl group having 1 to 3 carbon atoms.

The pantothenic acid compound of formula (V) is industrially available, and as such a pantothenic acid compound, for example, calcium pantothenate, sodium pantothenate, potassium pantothenate, and barium pantothenate can be employed.

The dialkylpropane derivative of formula (VI) which is another starting material for producing the pantothenic acid acetonide of formula (II) is industrially available, and as such a dialkylpropane derivative, for example, dimethoxy propane, diethoxy propane, and dipropoxy propane can be employed.

The desired pantothenic acid acetonide of formula (II) can be prepared by mixing the pantothenic acid compound of formula (V) and the dialkylpropane derivative of formula (VI).

It is preferable the above reaction be carried out in a solvent. Examples of such a solvent are hydrocarbons such as hexane, benzene, toluene, and xylene; ethers such as ethyl ether, tetrahydrofuran, and dioxane; acetone; dimethylformamide; and acetonitrile. These solvents can be used alone or in combination.

The reaction proceeds at temperatures in the range of 0° C. to 120° C., but it is preferable that the reaction be carried out at temperatures in the range of 20° to 90° C. in order to perform the reaction efficiently.

Furthermore, in order to increase the efficiency of the reaction, it is preferable that the reaction be carried out in the presence of an acid.

Specific examples of such an acid for use in the above reaction are oxalic acid, malonic acid, acetic acid, propionic acid, p-toluene sulfonic acid, benzene sulfonic acid, and benzoic acid. These acids can be used either alone or in combination.

It is preferable that the amount of such an acid be in the range of 0.1 to 2.2 equivalents to one equivalent of the pantothenic acid compound of formula (V).

Furthermore, in order to cause the reaction to proceed more efficiently, it is preferable to remove an alcohol produced in the course of the reaction. For this purpose, it is preferable to connect a Soxhlet extractor with Molecular Sieves incorporated therein to the reaction vessel for the above reaction.

Alternatively, the pantothenic acid acetonide of formula (II) can be prepared by replacing the dialkylpropane derivative of formula (VI) with an alkoxypropene derivative of the following formula (VII):

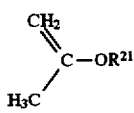

(VII)

wherein R²¹ is an alkyl group having 1 to 3 carbon atoms.

The alkoxypropene derivative of formula (VII) is industrially available, and as such an alkoxypropene derivative, for instance, 2-methoxypropene, 2-ethoxypropene, and 3-proxypropene can be employed.

EXAMPLE 2

[Preparation of pantothenic acid acetonide (3-[N-(2, 2,5,5-tetramethyl-1,3-dioxane-4-carbonyl)amino] propionic acid)]

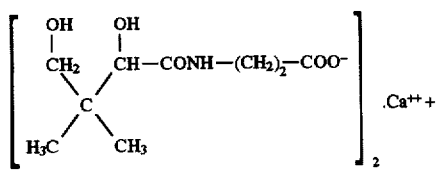

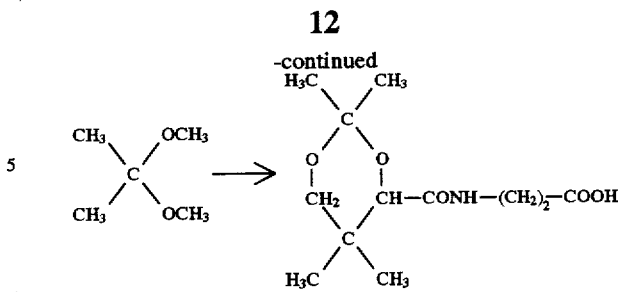

23.8 g (0.05 mol) of calcium pantothenate (3-[N-(2,4-dihydroxy-3,3-dimethyl-1-oxyobutyl)amino]calcium propionate), 4.5 g (0.05 mol) of oxalic acid, 15.6 g (0.15 mol) of 2,2-dimethoxypropane, and 1.9 (0.01 mol) of p-toluenesulfonic acid·one hydrate were suspended in 250 ml of acetone in a reaction vessel.

With a Soxhlet extractor with Molecular Sieves 4A incorporated therein being connected to the reaction vessel, the above reaction mixture was refluxed for 16 hours with the application of heat thereto, while methanol formed was eliminated during the course of the reaction.

After the completion of the reaction, solid components were removed from the reaction mixture, and the solvent was distilled away under reduced pressure. The thus obtained reside was dissolved in ethyl acetate and was then successively washed with water and with a saturated aqueous solution of sodium chloride.

An organic layer was separated from this mixture, and dried with anhydrous sodium sulfate.

The solvent was distilled away form the organic layer, and the residue was recrystallized from a mixed solvent composed of ethyl acetate and hexane, whereby pantothenic acid acetonide (3-[N-(2,2,5,5-tetramethyl-1,3-dioxane-4-carbonyl)amino]propionic acid) was obtained in the form of crystals in a yield of 19.0 g (73%).

Melting point: 110.2°–111.4° C.

¹H-NMR($\delta$, CDCl$_3$): 0.98(3H, s), 1.04(3H, s), 1.43(3H, s), 1.46(3H, s), 2.62(2H, t, J=7 Hz), 3.29(1H, d, J=12 Hz), 3.68(1H, d, J=12 Hz), 3.43–3.66(2H, m), 4.11(1H, s), 6.90–7.10(1H, m).

IR(v, KBr): 3420, 1734, 1636 cm$^{-1}$

Mass spectrometric analysis: Based on Molecular Formula $C_{12}H_{21}NO_5$ Calculated: 259. 1419 Found: 259. 1425

A urea derivative of the following formula (III), which serves as another starting material for producing the pantothenic acid derivative of formula (I) can be prepared by allowing a cyclohexanol derivative of formula (VIII) to react with the amine derivative of formula (IV) in accordance with the following reaction scheme:

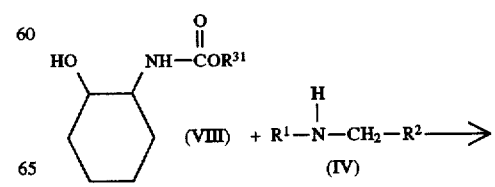

-continued

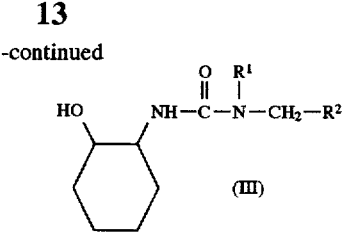

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, and $R^{31}$ is a phenyl group, a 4 nitrophenyl group, or a 2,4-dinitrophenyl group.

The cyclohexanol derivative of formula (VIII) is industrially available. Examples of such a cyclohexanol derivative are as follows:

2-(N-phenoxycarbonylamino)cyclohexanol,

2-[N-(4-nitrophenoxycarbonyl)amino]cyclohexanol, and

2-[N-(2,4-dinitrophenoxycarbonyl)amino]cyclohexanol.

Of the above-mentioned cyclohexanol derivatives, the following optical active cyclohexanol derivatives are particularly preferable for use in the present invention:

(1S, 2S)-2-(N-phenoxycarbonylamino)cyclohexanol, (1S, 2S)-2-[N-(4-nitrophenoxycarbonyl)amino] cyclohexanol, and (1S, 2S)-2-[N-(2,4-dinitrophenoxycarbonyl)amino] cyclohexanol.

The desired urea derivative of formula (III) can be prepared by mixing the cyclohexanol derivative of formula (VIII) and the amine derivative of formula (IX).

The above reaction be carried out either in the absence of a solvent or in the presence of a solvent. When the reaction is carried out in the presence of a solvent, inert solvents, for example, aromatic hydrocarbons such as benzene, toluene, and xylene; aliphatic hydrocarbons such as hexane and heptane; and ethers such as ether, THF, and dioxane can be employed.

The reaction proceeds at temperatures in the range of 30° C. to 150° C., but it is preferable that the reaction be carried out at temperatures in the range of 80° to 140° C. in order to perform the reaction efficiently.

EXAMPLE 3

[Preparation of (1S,2S)-2-(3-neopentyl-3-nonylureido)cyclohexanol]

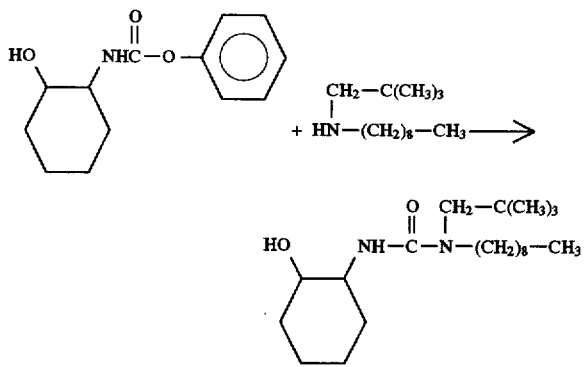

3.5 g (0.1 mol) of (1S, 2S)-2-N-phenoxycarbonyl-aminocyclohexanole, and 21.3 g (0.1 mol) of neopentyl-nonylamine were placed in a reaction vessel and were allowed to react with stirring at 120° C. for 2.5 hours. With the reaction mixture cooled with the addition of ice thereto, toluene was added to the reaction mixture.

An organic layer formed in the reaction mixture was separated therefrom and was successively washed with 1N-hydrochloric acid, water, 1N-sodium hydroxide aqueous solution (three times), and water (two times). The organic layer was then dried with anhydrous sodium sulfate.

The solvent was distilled away from the organic layer, whereby (1S,2S)-2-(3-neopentyl-3-nonylureido) cyclohexanol was obtained in a yield of 27.7 g (78%).

$^1$H-NMR($\delta$, CDCl$_3$): 0.88(3H, t, J=7 Hz), 0.95(9H, s), 1.16–1.36(16H, m), 1.50–2.18(6H, m), 2.40–2.60(3H, m), 2.95(1H, d, J=15 Hz), 3.11(1H, dd, J=15, 7 Hz), 3.19(1H, d, J=15 Hz), 3.30–3.40(1H, m), 3.42–3.54(1H, m).

EXAMPLE 4

[Preparation of (1S,2S)-2-(3-benzyl-3-decylureido) cyclohexanol]

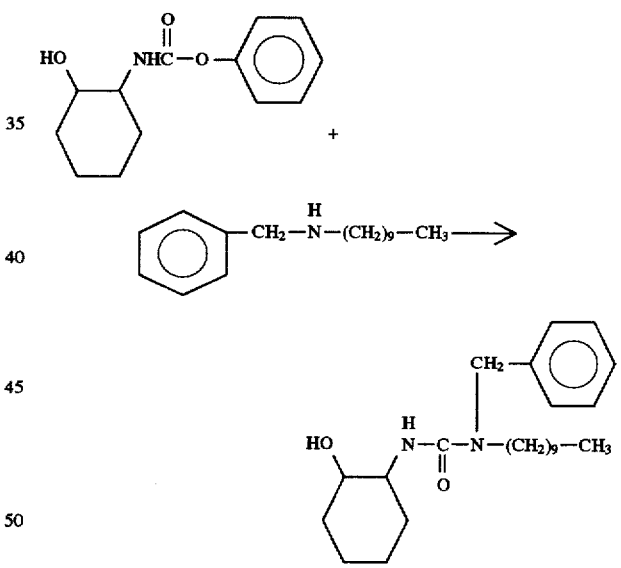

The same procedure for preparing (1S,2S)-2-(3-neopentyl-3-nonylureido)cyclohexanol as in Example 3 was repeated except that the neopentylnonylamine employed in Example 3 was replaced by benzyldecylamine, whereby (1S,2S)-2-(3-benzyl-3-decylureido)cyclohexanol was obtained in a yield of 85%.

$^1$H-NMR($\delta$, CDCl$_3$): 0.88(3H, t, J=7 Hz), 1.20–1.34(14H, m), 1.50–1.80(4H, m), 1.98–2.06(1H, m), 2.12–2.44(3H, m), 3.16–3.30(3H, m), 3.42–3.54(1H, m), 4.47(2H, s), 7.24–7.38(5H, m).

EXAMPLE 5

[Preparation of (1S,2S)-2-(3-decyl-3-isopropylureido)cyclohexanol]

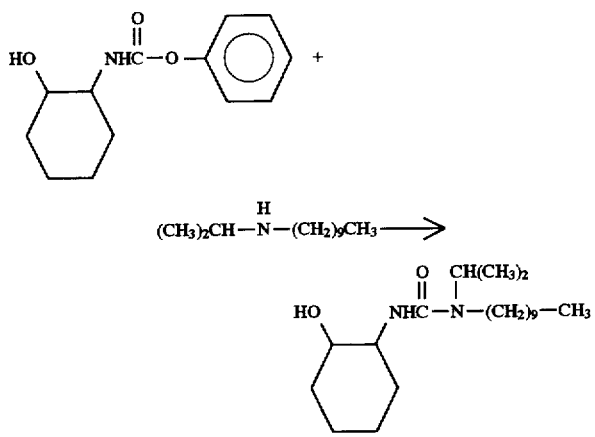

The same procedure for preparing (1S,2S)-2-(3-neopentyl-3-nonylureido)cyclohexanol as in Example 3 was repeated except that the neopentylnonylamine employed in Example 3 was replaced by decylisopropylamine, whereby (1S,2S)-2-(3-decyl-3-isopropylureido)cyclohexanol was obtained in a yield of 88%.

$^1$H-NMR($\delta$, CDCl$_3$): 0.88(3H, t, J=7 Hz), 1.13(6H, d, J=7 Hz), 1.20–1.34(15H, m), 1.48–2.10(6H, m), 3.01(2H, dd, J=6, 9 Hz), 3.28(1H, ddd, J=5, 11, 11 Hz), 3.44–3.56(1H, m), 4.20–4.40(2H, m).

The amine derivative of the following formula (IV) is a novel compound and is used as a starting material for producing the urea derivative of formula (III):

(IV)

wherein each R$^1$ and R$^2$ is different, and is a branched aliphatic hydrocarbon group having 3 to 5 carbon atoms, or a phenyl group; or a straight chain aliphatic hydrocarbon group having 5 to 10 carbon atoms.

Specific examples of the branched aliphatic hydrocarbon group having 3 to 5 carbon atoms represented by R$^{21}$ include an isopropyl group, an isobutyl group, a s-butyl group, a t-butyl group, an isopentyl group, a neopentyl group, and a t-pentyl group.

Specific examples of the straight chain aliphatic hydrocarbon group having 5 to 10 carbon atoms represented by R$^{22}$ include a pentyl group, a hexyl group, a heptyl group, an octyl group, a nonyl group, and a decyl group.

Specific examples of the amine derivative of formula (IV) include:

N-neopentyl-N-pentylamine,
N-hexyl-N-neopentylamine,
N-heptyl-N-neopentylamine,
N-octyl-N-neopentlamine,
N-neopentyl-N-nonylamine,
N-decyl-N-neopentylamine,
N-isoproyl-N-pentylamine,
N-hexyl-N-isopropylamine,
N-heptyl-N-isopropylamine,
N-isopropyl-N-octylamine,
N-isopropyl-N-nonylamine,
N-decyl-N-isopropylamine,
N-isopropyl-N-undecylamine,
N-benzyl-N-pentylamine,
N-benzyl-N-hexylamine,
N-benzyl-N-heptylamine,
N-benzyl-N-octylamine,
N-benzyl-N-nonylamine,
N-benzyl-N-decylamine,
N-t-butyl-N-pentylamine,
N-t-butyl-N-hexylamine,
N-t-butyl-N-heptylamine,
N-t-butyl-N-octylamine,
N-t-butyl-N-nonylamine, and
N-t-butyl-N-decylamine.

The amine derivative of formula (IV) can be prepared by a method comprising the steps of (Step 1) allowing a primary amine derivative of formula (X) to react with an aldehyde derivative of formula (XI) to produce an imine derivative of formula (XII), and (Step 2) reducing the imine derivative in accordance with the following reaction scheme:

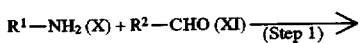

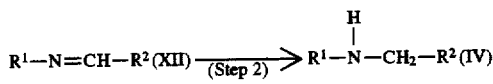

[Step 1]

In this step, the primary amine derivative of formula (X) is allowed to react with the aldehyde derivative of formula (XI), whereby the imine derivative of formula (XII) is produced.

In this step, the reaction can be carried out by mixing the primary amine derivative of formula (X) and the aldehyde derivative of formula (XI). When a solvent is used in this reaction, hydrocarbons such as hexane, benzene, toluene and xylene; halogenated hydrocarbons such as methylene chloride, chloroform, and carbon tetrachloride; and alcohols such as methanol and ethanol can be employed.

The reaction can be carried out at temperatures in the range of –20° C. to 150° C.

It is preferable that the reaction be carried out in the presence of an acid or a base. When an acid is employed, for example, sulfonic acids, such as benzene-sulfonic acid, and p-toluenesulfonic acid; and Lewis acids such as zinc chloride, boron trifluoride, and titanium chloride can be employed. When a base is employed, for example, sodium hydroxide, potassium hydroxide, potassium carbonate, and sodium carbonate can be employed.

The primary amine derivative of formula (X) employed in Step 1 are industrially available, and as such an primary amine derivative, for example, isopropylamine, isobutylamine, s-butylamine, t-butylamine, isopentylamine, neopentylamine, and t-pentylamine can be employed.

Examples of the aldehyde derivative of formula (XI) employed in Step 1 include hexanal, heptanal, octanal, nonanal, and decanal.

[Step 2]

In this step, the imine derivative of formula (XII) is reduced so that the amine derivative of formula (IV) is prepared.

This step is conducted in the atmosphere of hydrogen gas. The reduction can be carried out by catalytic reduction methods using noble metal catalysts, Raney nickel catalyst, and the like, and also by reduction methods using composite hydride compounds such as sodium cyanoboron hydride, sodium boron hydride; sodium, sodium amalgam, and electrolytic reduction.

It is preferable that this reduction reaction be carried out in a solvent. Examples of the solvent include alcohols such as methanol and ethanol; ethers such as tetrahydrofuran, dioxane and 1,2-dimethoxyethane; acetic acid, and water. These solvents may be employed alone or in combination.

Normally the reaction is conducted at room temperature.

EXAMPLE 6

[Preparation of N-nonylidene-N-neopentylamine]
$(CH_3)_3CCH_2NH_2+CH_3(CH_2)_7CHO\rightarrow(CH_3)_3CCH_2N\!=\!CH(CH_2)_7CH_3$ 14.2 g (0.1 mol) of nonanal was dropwise added to 8.7 g (0.1 mol) of neopentylamine, with stirring, while ice-cooled over a period of 1.5 hours. The reaction mixture was further stirred for 15 minutes. Toluene was added to this reaction mixture.

This reaction mixture was washed with a 6-N potassium hydroxide aqueous solution and an organic layer was separated from this mixture.

The organic layer was dried with anhydrous sodium sulfate, and the solvent was distilled away therefrom. N-nonylidene-N-neopentylamine was obtained from the residue by distillation in a yield of 17.35 g (82%).

Boiling point: 87° C./4 mmHg.

$^1$H-NMR($\delta$, CDCl$_3$): 0.88(3H, t, J=7 Hz), 0.90(9H, s), 1.20–1.36(10H, m), 1.45–1.58(2H, m), 2.20–2.30(2H, m), 3.12(2H, s), 7.57(1H, t, J=5 Hz)

EXAMPLE 7

[Preparation of N-neopentyl-N-nonylamine] $(CH_3)_3CCH_2N\!=\!CH(CH_2)_7CH_3\rightarrow(CH_3)_3CCH_2NH(CH_2)_8CH_3$ 10.5 g (0.05 mol) of N-nonylidene-N-neopentylamine was dissolved in methanol in a reaction vessel. With the addition of 1 g of a 10% palladium-carbon catalyst to the reaction mixture and the atmosphere in the reaction vessel replaced with hydrogen, the reaction mixture was vigorously stirred at room temperature for 18 hours.

After the completion of the reaction, the solid components were removed from the reaction mixture, and the solvent was distilled away from the residue, whereby N-neopentyl-N-nonylamine was obtained in a yield of 8.55 g (80%).

Melting point: 86° C./2 mmHg $^1$H-NMR($\delta$, CDCl$_3$): 0.88(3H, t, J=7 Hz), 0.92(9H, s), 1.24–1.34(12H, m), 1.44–1.74(3H, m), 2.35(2H, s), 2.60 (2H, t, J=7 Hz).

EXAMPLE 8

[Preparation of N-neopentylidene-N-nonylamine]
$(CH_3)_3CCHO+CH_3(CH_2)_8NH_2\rightarrow(CH_3)_3CCH\!=\!N(CH_2)_8CH_3$ 8.6 g (0.1 mol) of trimethylacetoaldehyde was dropwise added to 14.3 g (0.1 mol) of nonylamine, with stirring, while ice-cooled, over a period of 1.5 hours. The reaction mixture was further stirred for 15 minutes. Toluene was added to this reaction mixture.

This reaction mixture was washed with a 6-N potassium hydroxide aqueous solution and an organic layer was separated from this mixture.

The organic layer was dried with anhydrous sodium sulfate, and the solvent was distilled away therefrom. N-neopentylidene-N-nonylamine was obtained from the residue by distillation in a yield of 18.57 g (88%).

Boiling point: 92°–94° C./5 mmHg.

$^1$H-NMR($\delta$, CDCl$_3$): 0.88(3H, t, J=7 Hz), 1.06(9H, s), 1.20–1.36(12H, m), 1.50–1.80(2H, m), 3.34(2H, t, J=7 Hz), 7.48(1H,s).

EXAMPLE 9

[Preparation of N-neopentyl-N-nonylamine] $(CH_3)_3CCH_2N\!=\!CH(CH_2)_7CH_3\rightarrow(CH_3)_3CCH_2NH(CH_2)_8CH_3$ 18.57 g (0.087 mol) of N-nonylidene-N-neopentylamine was dissolved in methanol in a reaction vessel. With the addition of 1.86 g of a 10% palladium-carbon catalyst to the reaction mixture and the atmosphere in the reaction vessel replaced with hydrogen, the reaction mixture was vigorously stirred at room temperature for 18 hours.

After the completion of the reaction, the solid components were removed from the reaction mixture, and the solvent was distilled away from the residue, whereby N-neopentyl-N-nonylamine was obtained in a yield of 7.22 g (92%).

The boiling point and NMR measurement values of the thus obtained N-neopentyl-N-nonylamine were respectively the same as those of the N-neopentyl-N-nonylamine synthesized in Example 7.

What is claimed is:

1. A method of producing a pantothenic acid compound of formula (I):

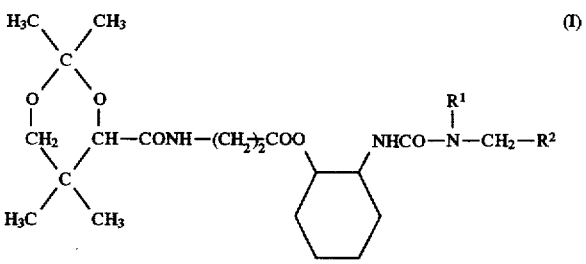

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, comprising the step of allowing a pantothenic acid acetonide of formula (II),

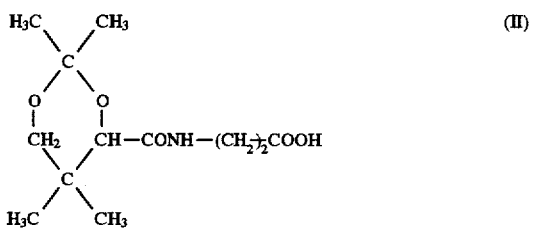

to react with a urea compound of formula (III),

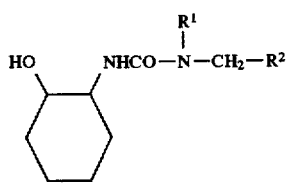 (III)

wherein $R^1$ and $R^2$ are respectively the same as defined in formula (I), in the presence of an acylating agent wherein said acylating agent is an acylating agent of formula (XIII), RX, wherein R is selected from the group consisting of a benzenesulfonyl group, a p-toluene-sulfonyl group, a methanesulfonyl group, ethoxycarbonyl group, and a phenoxycarbonyl group, and X is a halogen selected from the group consisting of a chlorine atom, a bromine atom, and an iodine atom.

2. The method of producing a pantothenic acid compound of formula (I) as claimed in claim 1, wherein said acylating of formula (XIII) is selected from the group consisting of benzenesulfonyl chloride, benzenesulfonyl bromide, benzenesulfonyl iodide, p-toluenesulfonyl chloride, p-toluenesulfonyl iodide, methanesulfonyl chloride, methanesulfonyl iodide, ethyl chloroformate, and phenyl chloroformate.

3. The method of producing a pantothenic acid compound of formula (I) as claimed in claim 1, wherein said urea compound of formula (III) is selected from the group consisting of:

2-(3-neopentyl-3-pentylureido)cyclohexanol,
2-(3-hexyl-3-neopentylureido)cyclohexanol,
2-(3-heptyl-3-neopentylureido)cyclohexanol,
2-(3-octyl-3-neopentylureido)cyclohexanol,
2-(3-neopentyl-3-nonylureido)cyclohexanol,
2-(3-decyl-3-neopentylureido)cyclohexanol,
2-(3-isoproyl-3-pentylureido)cyclohexanol,
2-(3-hexyl-3-isopropylureido)cyclohexanol,
2-(3-heptyl-3-isopropylureido)cyclohexanol,
2-(3-isopropyl-3-octylureido)cyclohexanol,
2-(3-isopropyl-3-nonylureido)cyclohexanol,
2-(3-decyl-3-isopropylureido)cyclohexanol,
2-(3-isopropyl-3-undecylureido)cyclohexanol,
2-(3-benzyl-3-pentylureido)cyclohexanol,
2-(3-benzyl-3-hexylureido)cyclohexanol,
2-(3-benzyl-3-heptylureido)cyclohexanol,
2-(3-benzyl-3-octylureido)cyclohexanol,
2-(3-benzyl-3-nonylureido)cyclohexanol,
2-(3-benzyl-3-decylureido)cyclohexanol,
2-(3-t-butyl-3-pentylureido)cyclohexanol,
2-(3-t-butyl-3-hexylureido)cyclohexanol,
2-(3-t-butyl-3-heptylureido)cyclohexanol,
2-(3-t-butyl-3-octylureido)cyclohexanol,
2-(3-t-butyl-3-nonylureido)cyclohexanol, and
2-(3-t-butyl-3-decylureido)cyclohexanol.

4. A method of producing an amine compound of formula (IV):

 (IV)

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, comprising the steps of:

(a) allowing a primary amine of formula (X) to react with an aldehyde compound of formula (XI) to produce an imine compound of formula (XII) in step 1, and (b) reducing said imine compound in step 2 in accordance with the following reaction scheme:

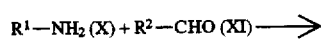

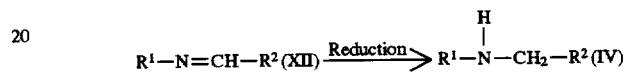

wherein $R^1$ and $R^2$ are the same as defined in formula (IV).

5. The method of producing an amine compound of formula (IV) as claimed in claim 4, wherein said primary amine of formula (X) employed in step 1 is selected from the group consisting of isopropylamine, isobutylamine, s-butylamine, t-butylamine, isopentyl-amine, neopentyl-amine, and t-pentylamine.

6. A method of producing an imine compound of formula (XII),

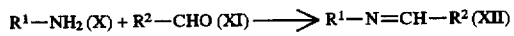

wherein each of $R^1$ and $R^2$ is different, and is a branched aliphatic hydrocarbon group having 3 to 5 carbon atoms, or a phenyl group; or a straight chain aliphatic hydrocarbon group having 5 to 10 carbon atoms, comprising the step of allowing a primary amine (X) to react with an aldehyde compound of formula (XI) in accordance with the following reaction scheme:

wherein $R^1$ and $R^2$ are respectively the same as defined in formula (XIII).

7. The method of producing an imine compound of formula (XII) as claimed in claim 6, wherein said primary amine of formula (X) is selected from the group consisting of isopropylamine, isobutylamine, s-butylamine, t-butylamine, isopentyl-amine, neopentyl-amine, and t-pentylamine.

* * * * *